(12) United States Patent
Brodsky

(10) Patent No.: US 10,993,979 B2
(45) Date of Patent: May 4, 2021

(54) BOTANICAL TINCTURES

(71) Applicant: The Trustees of Columbia University in the City of New York, New York, NY (US)

(72) Inventor: Marc Brodsky, Stamford, CT (US)

(73) Assignee: The Trustees of Columbia University, New York, NY (US)

(*) Notice: Subject to any disclaimer, the term of this patent is extended or adjusted under 35 U.S.C. 154(b) by 83 days.

(21) Appl. No.: 16/190,545

(22) Filed: Nov. 14, 2018

(65) Prior Publication Data

US 2019/0151388 A1 May 23, 2019

Related U.S. Application Data

(60) Provisional application No. 62/588,526, filed on Nov. 20, 2017.

(51) Int. Cl.
| | |
|---|---|
| *A61K 36/00* | (2006.01) |
| *A61K 36/288* | (2006.01) |
| *A61K 36/235* | (2006.01) |
| *A61K 36/232* | (2006.01) |
| *A61K 36/54* | (2006.01) |
| *A61K 36/752* | (2006.01) |
| *A61K 36/9068* | (2006.01) |
| *A61K 36/484* | (2006.01) |
| *A61K 36/28* | (2006.01) |

(52) U.S. Cl.
CPC .......... *A61K 36/288* (2013.01); *A61K 36/232* (2013.01); *A61K 36/235* (2013.01); *A61K 36/28* (2013.01); *A61K 36/484* (2013.01); *A61K 36/54* (2013.01); *A61K 36/752* (2013.01); *A61K 36/9068* (2013.01); *A61K 2236/333* (2013.01)

(58) Field of Classification Search
CPC ..................................................... A61K 36/00
See application file for complete search history.

(56) References Cited

U.S. PATENT DOCUMENTS

| | | |
|---|---|---|
| 7,985,433 B2 | 7/2011 | Kuper et al. |
| 9,468,865 B1 | 10/2016 | Young et al. |
| 2016/0228787 A1 | 8/2016 | Payack |
| 2016/0250157 A1 | 9/2016 | Keaffaber et al. |

FOREIGN PATENT DOCUMENTS

| | | |
|---|---|---|
| WO | 2009/115701 A3 | 3/2010 |
| WO | 2016/078144 A1 | 5/2016 |

OTHER PUBLICATIONS

English machine translation of Wang et al., CN 105727089 A, Jul. 2016.*

(Continued)

*Primary Examiner* — Rosanne Kosson
(74) *Attorney, Agent, or Firm* — Occhiuti & Rohlicek LLP

(57) ABSTRACT

Disclosed herein are botanical tinctures that can be variously formulated and packaged and used as dietary supplements and in the prevention and treatment of symptoms associated with disorders affecting digestion or the digestive tract (e.g., symptoms of functional gastrointestinal disorders, FGIDs).

16 Claims, 1 Drawing Sheet

(56) References Cited

OTHER PUBLICATIONS

Bayer. (Oct. 2013-Oct. 2017). A Double-blind, Randomised, Placebo-controlled Study on the Efficacy of Iberogast® (STW5) in Patients With Irritable Bowel Syndrome. Identifier NCT01940848. https://clinicaltrials.gov/ct2/show/study/NCT01940848.
Rahimi, Roja, "Herbal medicines for the management of irritable bowel syndrome: A comprehensive review." World Journal of Gastroenterology, vol. 18, No. 7, pp. 589-600, Feb. 2012.
Guo, Bao-Jian et al. "Biological and clinical implications of herbal medicine and natural products for the treatment of nflammatory bowel disease." Annals of the New York Academy of Sciences, vol. 1401, No. 1, pp. 37-48, 2017.. doi:10.1111/nyas.13414.
Gerson, Lauren B. "The tincture of time and irritable bowel syndrome symptoms." Gastroenterology vol. 140, No. 5, pp. 1680-1682, 2011. doi:10.1053/j.gastro.2011.03.035.
Holtmann, Gerald, "Herbal Medicines for the Treatment of Functional and Inflammatory Bowel Disorders." Clinical Gastroenterology and Hepatology, vol. 13, No. 3, pp. 422-432, 2015.
Di Giorgio, C et al. "In vitro and in vivo antimutagenic effects of DIG, a herbal preparation of Berberis vulgaris, Taraxacum officinale and Arctium lappa, against mitomycin C." Journal of natural medicines vol. 69, No. 3, pp. 267-277, 2015. doi:10.1007/s11418-015-0886-8.
Fan, Heng, "Tongxie Formula Reduces Symptoms of Irritable Bowel Syndrome," Clinical Gastroenterology and Hepatology, vol. 15, No. 11, pp. 1724-1732, Nov. 2017.

\* cited by examiner

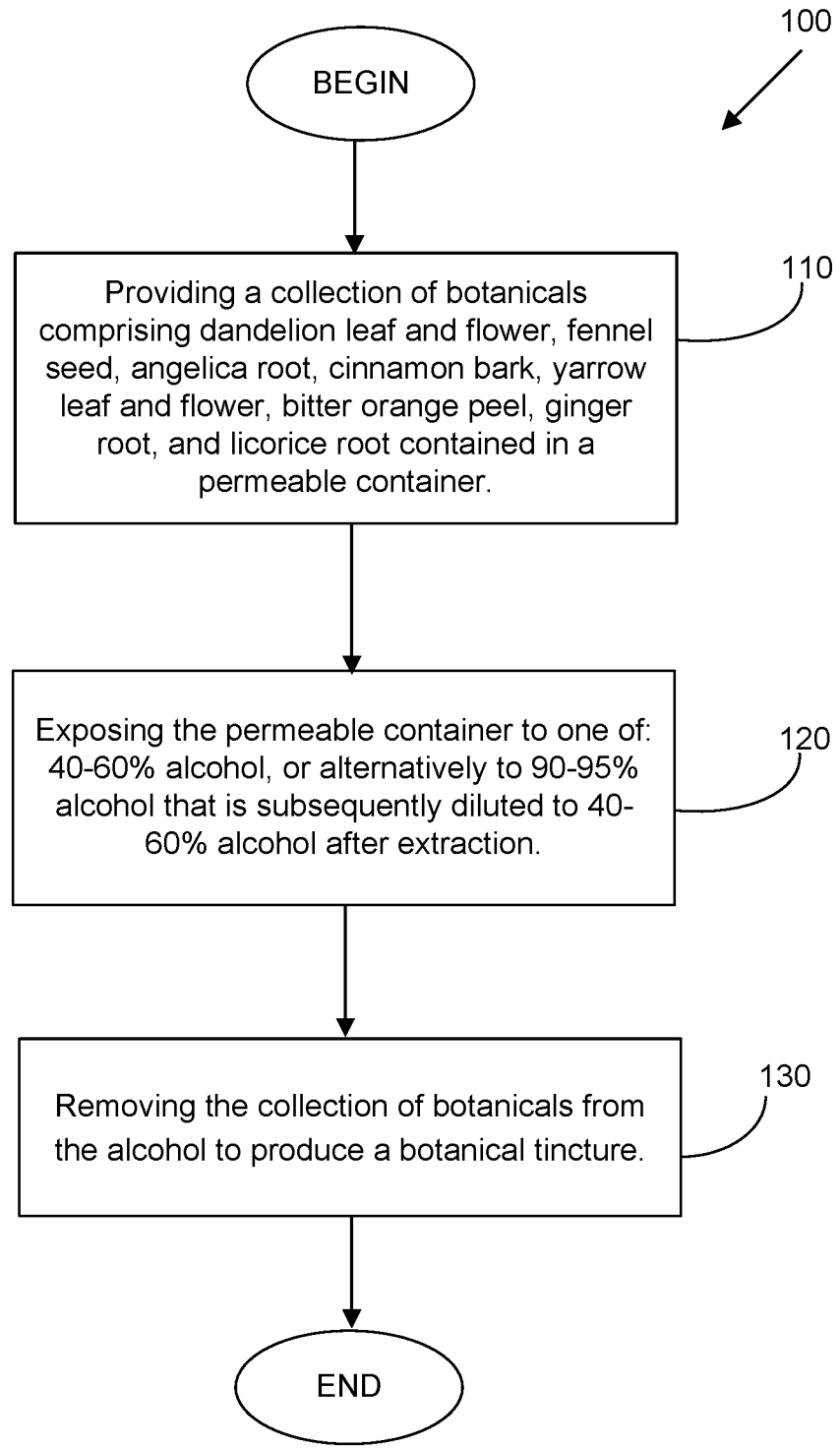

BOTANICAL TINCTURES

CROSS-REFERENCE TO RELATED APPLICATIONS

This application claims the benefit of U.S. Provisional Application No. 62/588,526, entitled "BOTANICAL TINCTURES" and filed Nov. 20, 2017, the content of which is incorporated herein by reference in its entirety.

BACKGROUND

Chinese medicine has evolved over thousands of years and incorporates the use of Chinese herbal medicines (CHMs) and various practices, such as acupuncture; tui na manipulative therapy; and qi gong and tai chi mind-body stretching exercises. In the United States and elsewhere, people are increasingly using CHMs as dietary supplements and engaging in other practices, such as those just mentioned, to complement pharmaceutical medications.

SUMMARY

Provided herein are botanical tinctures that can be variously formulated and packaged and used as dietary supplements to prevent (e.g., reduce the risk of) and provide relief of symptoms of disorders that adversely affect the alimentary canal. These disorders can be a functional gastrointestinal disorder (FGID), such as Irritable Bowel Syndrome (IBS) or Functional Dyspepsia. These disorders can cause debilitating symptoms such as abdominal pain, cramps, fullness, bloating, and nausea. More specifically, described herein are botanical tinctures comprising extracts of dandelion root and leaf, fennel seed, *angelica* root, cinnamon bark, yarrow leaf and flower, bitter orange peel, ginger root, and licorice root. The extracts can be suspended in an alcohol distillate of, for example, about 40-60% alcohol, and the extracts can be present in the tinctures in amounts that reduce the risk of developing symptoms of a disorder that adversely affects the alimentary canal (e.g., an FGID) or alleviate a symptom once it occurs. In some embodiments, the tincture comprises about 20% by volume extract of dandelion root and leaf. In this embodiment and any of the others described herein, the tincture can further comprise about 10% by volume fennel seed; about 10% by volume *angelica* root; about 15% by volume cinnamon bark; about 10% by volume yarrow leaf and flower; about 10% by volume bitter orange peel; about 10% by volume ginger root; and about 15% by volume licorice root. By "about," we mean plus-or-minus 10%. Thus, about 20% encompasses 18% to 22%.

Also described are methods of making a botanical tincture, the methods comprising:

a) providing a collection of botanicals comprising dandelion root and leaf, fennel seed, *angelica* root, cinnamon bark, yarrow leaf and flower, bitter orange peel, ginger root, and licorice root contained in a permeable container;

b) exposing the permeable container to about 40-60% alcohol; and c) removing the collection of botanicals from the alcohol, thereby producing a botanical tincture.

In some embodiments, the method may optionally further include aging the botanical tincture.

The collection of botanicals and the alcohol can be exposed to one another in a ratio of 1 part botanicals:5 parts alcohol. Exposing the permeable container to 40-60% alcohol can be accomplished by exposing each gram of the collection of botanicals to 5 mls of the alcohol.

Alternatively, the eight botanicals may be mixed together in a permeable container and extracted at 90-95% at a ratio of 1 part botanical:5 parts alcohol and then be diluted to 40-60% alcohol.

Also described are methods of reducing the risk that a subject will develop symptoms of FGIDs or alleviate a symptom of that condition. These methods can include a step of administering an effective amount of a botanical tincture as described herein. The person using the tincture may have been diagnosed as having an FGID-related symptoms described herein.

Other features and advantages of the invention are apparent from the following description and drawing, and from the claims.

BRIEF DESCRIPTION OF THE DRAWINGS

These and other aspects will now be described in detail with reference to the following drawings.

FIG. 1 is a flowchart of an example procedure to make a botanical tincture.

DETAILED DESCRIPTION

Described herein are botanical tinctures, which may also be referred to as dietary supplement, herbal combination preparations, or phytopharmaceutical products. The botanical tinctures can be administered to any human subject, regardless of that subject's health status, but may be especially useful in reducing the risk of or improving symptoms caused by a FGID that adversely affects the alimentary canal. The active ingredients of these phytopharmaceutical products are preparations of dried plants or parts of plants as ethanolic liquid extracts.

The compositions can include a mixture of eight herbal extracts, as follows:

| Common Name | Scientific Name | Chinese Herbal Medicine (CHM) Name |
| --- | --- | --- |
| Dandelion root and leaf | *Taraxacom Officinale* | Pu Gong Ying |
| Fennel seed | *Foeniculum vulgare* | Xiao Hui Xiang |
| Angelica root | *Angelica Sinensis* | Dang Gui |
| Cinnamon bark | *Cinnamomum Verum* | Gui Zhi |
| Yarrow leaf and flower | *Achillea Millefolium* | Ya Luo |
| Bitter Orange peel | *Citrus Aurantium* | Zhi Ke |
| Ginger root | *Zingiber Officinale* | Gan Jiang |
| Licorice root | *Radix Glycyrrhizae* | Gan Cao |

All 8 botanicals are classified as Generally Recognized As Safe (GRAS) by the United States Food and Drug Administration (FDA). These botanical extracts are all approved by German Commission E (the German equivalent of the United States FDA).

The production processes and content of each ingredient is reproducible and standardized. The compositions described herein may also be prepared in pill or powder tea form.

The eight botanicals can be mixed together in a permeable container (e.g., a mesh bag or strainer) and extracted in 40-60% alcohol at a ratio of 1 part botanical:5 parts alcohol, w/v (e.g., 1 g botanicals/5 ml alcohol). The botanicals can be removed from the alcohol after a period of weeks (e.g., after one to four weeks). Alternatively, the eight botanicals may be mixed together in a permeable container and extracted at 90-95% at a ratio of 1 part botanical:5 parts alcohol and then be diluted to 40-60% alcohol.

In one embodiment, the production method produces a botanical tincture that comprises the following ingredients in the following relative amounts:

| Common Name | Scientific Name | Chinese Herbal Medicine (CHM) Name | % Volume/ Botanical |
|---|---|---|---|
| Dandelion Root and Leaf | *Taraxacom Officinale* | Pu Gong Ying | 20 |
| Fennel Seed | *Foeniculum vulgare* | Xiao Hui Xiang | 10 |
| Angelica Root | *Angelica Sinensis* | Dang Gui | 10 |
| Cinnamon Bark | *Cinnamomum Verum* | Gui Zhi | 15 |
| Yarrow Leaf and Flower | *Achillea Millefolium* | Ya Luo | 10 |
| Bitter Orange Peel | *Citrus Aurantium* | Zhi Ke | 10 |
| Ginger Root | *Zingiber Officinale* | Gan Jiang | 10 |
| Licorice Root | *Radix Glycyrrhizae* | Gan Cao | 15 |
| Total | | | 100 |

While the present compositions are not limited by the mechanisms of action of any one or more of the ingredients, dandelion (pu gong ying) may serve as the "King herb" to "clear heat and resolve dampness." Dandelion root and leaf constituents are sesquiterpene lactones, believed to exert anti-inflammatory effects; phenylpropanoids, believed to have inflammation-modulating effects; triterpenoid saponins that in other botanicals are adaptogenic; polysaccharides, and inulin, a dietary fiber. Sesquiterpene lactones give a bitter taste to leaves.

With regard to dosage, a subject or patient may take 2-5 ml of the botanical tincture 1-3 times/day (i.e., 2-15 mls per day, e.g., 2.5 ml per day). As noted, in some embodiments, the same botanical proportions described herein that are used for preparing tinctures may also be used to present the formulation in a pill or powdered tea form.

Fennel seed contains trans-anethole (50-70%), (+)-fenchone (9-22%), and estragole [methyl chavicol] (25%). Other compounds in the oil include anisaldehyde, camphene, fenchyl alcohol, limonene, ρ-anisic acid, 3-carene, ρ-cymene, α-fenchene, β-myrcene, α-pinene, β-pinene, α-phellandrene, sabinene, α- and β-terpinene, γ-terpinene, terpinolene, α-thujene, cis- and trans-ocimenes, trans-1,8-terpin.

Fennel seed's therapeutic uses have been introduced and integrated into many other systems of traditional medicine, including Ayurvedic, Chinese, and Japanese Kampo.

*Angelica* root contains phellandrene, terpenes, coumarin and coumarin derivatives (a total of 26 derivatives have been identified) such as osthol, angelicin and archangelicin. The root also contains bitter substances, glucose, sucrose, saccharine and some organic acids like aconitic acid, fumaric acid, and oxalic acid.

Cinnamon bark contains volatile oils (1-4%) of cinnamaldehyde (60-80%), eugenol (up to 10%) and trans-cinnamic acid (5-10%); phenolic compounds (4-10%), condensed tannins, catechins, and proanthocyanidins; monoterpenes and sesquiterpenes (pinene); calcium-monoterpenes oxalate; gum; mucilage; resin, starch, sugars, and traces of coumarin.

Yarrow leaf and flower contains 34% condensed and hydrolysable tannins; 0.31.4% volatile oils, mostly linalool, borneol, camphor, b-caryophyllene, 1,8-cineole, and sesquiterpene lactones composed of guaianolides, mainly achillicin (a proazulene), achillin, leucodin, and germacranolides (dihydroparthenolide, achillifolin, millefin); flavonoids (apigenin, luteolin, isorhamnetin, rutin); amino acids (alanine, histidine, leucine, lysine); fatty acids (linoleic, palmitic, oleic); phenolic acids (caffeic, salicylic); vitamins (ascorbic acid, folic acid); alkaloids and bases (achiceine, achilleine, betaine, choline); alkanes (tricosane); polyacetylenes; saponins; sterols (b-sitosterol); sugars (dextrose, glucose, mannitol, sucrose); and coumarins.

Bitter orange peel contains bitter tasting flavonoid glycosides including neohesperidin and naringin; nonbitter flavonoids, such as hesperidin, rutoside, sinensetin, nobiletin, tangeretin; between 1-2% essential oil with limonene as the main component (>90%), perillyl alcohol and geraniol; pectins; and furanocoumarins. There are also phenols contained in the peel including polymethoxylated flavones.

Ginger root contains oleoresin (4.0-7.5%) composed of non-volatile pungent principles (phenols such as gingerols and their related dehydration products shogaols), non-pungent substances (fats and waxes), and volatile oils; volatile oil (1.0-3.3%), of which 30-70% are sesquiterpenes, mainly β-bisabolene, (−)-zingiberene, β-sesquiphellandrene, and (+)-ar-curcumene, and monoterpenes, mainly geranial and neral; carbohydrates, mainly starch (40-60%); proteins (9-10%); lipids (6-10%) composed of triglycerides, phosphatidic acid, lecithins, and free fatty acids; vitamins niacin and A; minerals; and amino acids.

Licorice root major constituents are triterpene saponins. Glycyrrhizin (glycyrrhizic acid, glycyrrhizinic acid) is the major component (2-9%); minor components occur in proportions that vary depending on the species and geographical location. Glycyrrhizin occurs as a mixture of potassium and calcium salts. It is a monodesmoside, which on hydrolysis releases two molecules of D-glucuronic acid and the aglycone glycyrrhetic (glycyrrhetinic) acid (enoxolone). Glycyrrhizin is generally regarded as the active principle of Radix Glycyrrhizae and is responsible for its sweetness, which is 50 times that of sucrose. Flavonoid constituents include liquiritigenin and isoliquiritigenin.

The compositions can be further generated according to the following specifications:

| Common Name | Scientific Name | CHM Name | g Botanical/ 50 Liter 50% alcohol (1:5) | Percent Solute | mg Botanical/ml |
|---|---|---|---|---|---|
| Dandelion leaf and flower | *Taraxacom Officinale* | Pu Gong Ying | 2000 | 20 | 40 |
| Fennel seed | *Foeniculum vulgare* | Xiao Hui Xiang | 1120 | 10 | 10 |
| Angelica root | *Angelica Sinensis* | Dang Gui | 1120 | 10 | 30 |
| Cinnamon bark | *Cinnamomum Verum* | Gui Zhi | 1400 | 15 | 30 |
| Yarrow leaf and flower | *Achillea Millefolium* | Ya Luo | 1120 | 10 | 20 |
| Bitter orange peel | *Citrus Aurantium* | Zhi ke | 1120 | 10 | 10 |
| Ginger root | *Zingiber Officinale* | Gan Jiang | 1120 | 10 | 30 |
| Licorice root | *Radix Glycyrrhizae* | Gan Cao | 1400 | 15 | 30 |
| Total | | | 10000 (10 kg) | 100 | 200 |

Following exposure of the collection of botanicals to alcohol, the botanical tincture can be stored (e.g., aged in barrels (e.g., oak barrels)) for a period of time (e.g., about 2-24 months, e.g., about 18 months).

In use, the compositions described herein can be administered as nutritional supplements and prophylactic treatments to subjects (e.g., humans) for reducing the risk of a disorder that adversely affects the alimentary canal or for treating the symptoms once present. Thus, the present methods encompass reducing the risk of developing an FGID, such as IBS, or treating a symptom once present.

With reference to FIG. 1, a flowchart of an example procedure 100 to make a botanical tincture (such as the botanical tinctures described herein) is shown. The procedure 100 includes providing 110 a collection of botanicals comprising dandelion leaf and flower, fennel seed, *angelica* root, cinnamon bark, yarrow leaf and flower, bitter orange peel, ginger root, and licorice root contained in a permeable container. In some embodiments, the collection of botanicals and the alcohol may be exposed to one another at a ratio of 1 part botanicals:5 parts alcohol.

The procedure 100 additionally includes exposing 120 the permeable container to one of 40-60% alcohol, or alternatively to 90-95% alcohol, which is then diluted to 40-60% alcohol after extraction. In some embodiments, exposing the permeable container to 40-60% alcohol may include exposing each gram of the collection of botanicals to 5 mls of the alcohol. Alternatively, exposing the permeable container to 90-95% alcohol may include exposing each gram of the collection of botanicals to 5 mls of the alcohol and then diluting to 40-60% alcohol after extraction.

The procedure 100 further includes removing 130 the collection of botanicals from the alcohol, to thus produce a botanical tincture. In some variations, the procedure may optionally further include aging the botanical tincture.

In some embodiments, a procedure of reducing the risk that a subject will develop a disorder that adversely affects the alimentary canal or alleviating a symptom of the disorder is provided. The procedure includes administering an effective amount of the botanical tincture comprising extracts of dandelion root and leaf, fennel seed, *angelica* root, cinnamon bark, yarrow leaf and flower, bitter orange peel, ginger root, and licorice root. The patient may have been diagnosed as having a functional gastrointestinal disorder (FGID). FGID may include diagnosis of Irritable Bowel Syndrome (IBS) and/or functional dyspepsia. As noted, in some examples, the extracts are suspended in a 40-60% alcohol distillate. The extracts may be present in amounts that alleviate a symptom associated with an FGID. As also noted, the tincture may include 20% by volume extract of dandelion root and leaf. The tincture may further include 10% by volume fennel seed, 10% by volume *angelica* root, 15% by volume cinnamon bark, 10% by volume yarrow leaf and flower, 10% by volume bitter orange peel, 10% by volume ginger root, and 15% by volume licorice root.

In some instances, the compositions can be, but are not necessarily only, administered before the patient reclines for sleep or soon before or after a meal. The compositions can be administered in an amount and for a time sufficient to reduce the likelihood of developing symptoms or to provide relief from a symptom. The symptoms include but are not limited to altered bowel consistency combined with abdominal pain that is usually relieved with a bowel movement, a feeling of indigestion, or symptoms of discomfort with fullness, bloating, and possibly nausea associated with meals. As with other indications, a composition as described herein can be administered together with an antacid or other medication (e.g., a medication that may reduce the production of acid in the stomach and/or reduce inflammation in the esophagus).

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±10%, ±5%, or +0.1% from the specified value, as such variations are appropriate in the context of the compositions, devices, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the compositions, methods, devices, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only, and is not intended to be limiting with respect to the scope of the appended claims, which follow. Features of the disclosed embodiments can be combined, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

What is claimed is:

1. A botanical tincture comprising therapeutically effective amounts of extracts of dandelion root and leaf, fennel seed, *angelica* root, cinnamon bark, yarrow leaf and flower, bitter orange peel, ginger root, and licorice root.

2. The botanical tincture of claim 1, wherein the extracts are suspended in a 40-60% aqueous alcohol distillate.

3. The botanical tincture of claim 1, wherein the extracts are present in amounts that alleviate a symptom associated with a functional gastrointestinal disease (FGID).

4. The botanical tincture of claim 1, wherein the tincture comprises 20% by volume extract of dandelion root and leaf.

5. The botanical tincture of claim 4, wherein the tincture further comprises 10% by volume fennel seed extract: 10% by volume *angelica* root extract: 15% by volume cinnamon bark extract; 10% by volume yarrow leaf and flower extract: 10% by volume bitter orange peel extract, 10% by volume ginger root extract; and 15% by volume licorice root extract.

6. A method of making the botanical tincture of claim 1, the method comprising:
   a) providing a collection of botanicals comprising dandelion leaf and flower, fennel seed, *angelica* root, cinnamon bark, yarrow leaf and flower, bitter orange peel, ginger root, and licorice root contained in a permeable container;

b) submerging the collection of botanicals in step (a) in the permeable container in one of: 40-60% aqueous alcohol, or 90-95% aqueous alcohol that is subsequently diluted to 40-60% aqueous alcohol after extraction; and c) removing the collection of botanicals from the aqueous alcohol to produce a botanical tincture.

7. The method of claim 6, further comprising aging the botanical tincture.

8. The method of claim 6, wherein the collection of botanicals and the aqueous alcohol are at a ratio of 1 part botanicals:5 parts aqueous alcohol.

9. The method of claim 6, wherein 1 g of the collection of botanicals is extracted with 5 g of the 40-60% aqueous alcohol, or wherein 1 g of the collection of botanicals is extracted with 5 g of the 90-95% aqueous alcohol, followed by diluting the aqueous alcohol to 40-60% after extraction.

10. A method of reducing the risk that a subject will develop a disorder that adversely affects the alimentary canal or of alleviating a symptom of the disorder, the method comprising administering an effective amount of the botanical tincture of claim 1 to a patient in need thereof.

11. The method of claim 10, wherein the extracts are suspended in a 40-60% aqueous alcohol distillate.

12. The method of claim 10, wherein the extracts are present in amounts that alleviate a symptom associated with a functional gastrointestinal disease (FGID).

13. The method of claim 10, wherein the tincture comprises 20% by volume of the extract of dandelion root and leaf.

14. The method of claim 13, wherein the tincture comprises 10% by, volume fennel seed extract; 10% by volume *angelica* root extract; 15% by volume cinnamon bark extract; 10% by volume yarrow leaf and flower extract: 10% by volume bitter orange peel extract, 10% by volume ginger root extract; and 15% by volume licorice root extract.

15. The method of claim 10, wherein the patient has been diagnosed as having a functional gastrointestinal disorder (FGID).

16. The method of claim 15, wherein the FGID includes diagnosis of Irritable Bowel Syndrome (IBS) and/or functional dyspepsia.

* * * * *